United States Patent [19]

Chodnekar et al.

[11] 4,234,598
[45] Nov. 18, 1980

[54] PHENYLCARBAMATES

[75] Inventors: Madhukar S. Chodnekar, Seltisberg; Peter Loeliger, Münchenstein; Ulrich Schwieter, Reinach; Albert Pfiffner, BUMLu/ lach; Milos Suchy, Pfaffhausen; René Zurflün, Bülach, all of Switzerland

[73] Assignee: Hoffmann-La Roche Inc., Nutley, N.J.

[21] Appl. No.: 29,088

[22] Filed: Apr. 11, 1979

Related U.S. Application Data

[63] Continuation of Ser. No. 816,826, Jul. 18, 1977, abandoned.

[51] Int. Cl.$^3$ .................... A01N 43/24; C07D 319/08
[52] U.S. Cl. .............................. 424/278; 260/340.3
[58] Field of Search ...................... 260/340.3; 424/278

[56] References Cited

U.S. PATENT DOCUMENTS

| | | | |
|---|---|---|---|
| 3,306,913 | 2/1967 | Augstein et al. | 260/340.3 |
| 3,455,912 | 7/1969 | Eitel et al. | 260/340.3 |
| 3,829,441 | 8/1974 | Nicholson | 260/340.3 |

Primary Examiner—Ethel G. Love
Attorney, Agent, or Firm—Jon S. Saxe; Bernard S. Leon; William M. Farley

[57] ABSTRACT

Phenylcarbamates of the general formula:

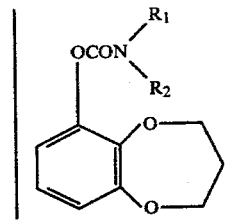

wherein $R_1$ is lower alkyl, lower alkenyl, lower alkynyl, lower alkylcarbonyl, halogen-lower alkylcarbonyl or trichloromethylsulfenyl and $R_2$ is hydrogen or lower alkyl, processes for their preparation; pesticidal compositions containing one or more of the phenylcarbamates as the active ingredient and methods for using the pesticide composition are disclosed.

18 Claims, No Drawings

PHENYLCARBAMATES

This is a continuation, of application Ser. No. 816,826 filed July 18, 1977, and now abandoned.

DETAILED DESCRIPTION OF THE INVENTION

The invention is directed to phenylcarbamates of the general formula

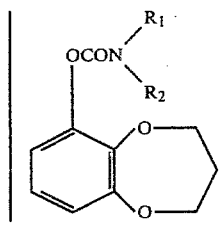

wherein $R_1$ is lower alkyl, lower alkenyl, lower alkynyl, lower alkylcarbonyl, halogen-lower alkylcarbonyl or trichloromethylsulfenyl and $R_2$ is hydrogen or lower alkyl and processes for their preparation.

This invention is also directed to compositions effective for pest control, and especially for insect control, which contain, as the active component, one or more compounds of the general formula I. Finally, this invention is directed to processes for the preparation of such compositions as well as methods for their use.

The compounds of formula I are prepared by the several procedures detailed below.

Procedure A

A compound of the formula

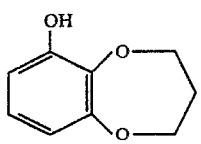

is reacted in the presence of a base, with an isocyanate of the formula $$R_3\text{—NCO} \qquad \text{III}$$

wherein $R_3$ is lower alkyl, lower alkenyl or lower alkynyl.

Using this procedure, a compound of formula II is dissolved in an inert solvent such as, for example, ether, benzene, methylene chloride or tetrahydrofuran. An amount of base equal to at least a catalytic amount is then added to the solution. Representative bases include, for example, potassium carbonate, triethylamine, quinoline and pyridine. Pyridine is preferred since it can be used both as the solvent and as the catalyst. The isocyanate compound is then added stepwise to the solution. Reaction temperatures can range from about 0° C. to about 40° C. with room temperature (20°-25° C.) preferred. Pressure is not a critical variable.

Procedure B

A compound of the formula

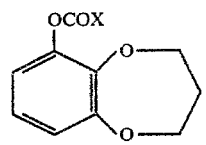

wherein X is chlorine, bromine or iodine, is reacted with a compound of the formula

wherein $R_4$ is lower alkyl, lower alkenyl or lower alkynyl and $R_5$ is hydrogen or lower alkyl.

A starting material of formula IV is reacted with an amine of formula V in an inert solvent. Representative inert solvents include ether, preferably diethyl ether, dimethylformamide, a chlorinated hydrocarbon solvent, preferably methylene chloride or chloroform, dimethylsulphoxide and benzene. Reaction temperature can range from about 0° C. to the boiling point of the particular reaction mixture. A temperature range between about 15° C. and 40° C. is especially preferred. Pressure is not a critical variable.

If the amine used is in the form of a salt such as, e.g., the hydrohalogenide, a weak base such as potassium carbonate can be added to the reaction mixture.

Upon completion of the reaction, the solvent is removed and the product is obtained by recrystallization of the resulting residue.

Compounds of formula IV, which are the starting material for this Procedure are novel compounds. They are prepared by, for example, dissolving a phenol of formula II in an inert solvent such as ether or benzene and adding thereto a compound of the formula $$X_2COX_1$$

wherein $X_1$ and $X_2$ are chlorine, bromine or iodine and, preferably, chlorine.

The reaction is preferably carried out between 0° C. and 20° C. The product, i.e., a compound of formula IV, is, for purposes of Procedure B, not isolated but reacted in situ with an amine of formula V.

Procedure C

A compound of the formula

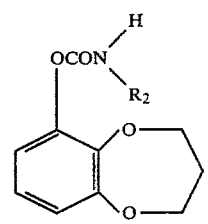

wherein $R_2$ is hydrogen or lower alkyl is reacted, in the presence of a base, with a compound of the general formula $$R_6\text{—}(CH_2)_m\text{—COY} \qquad \text{VII}$$

wherein R$_6$ is hydrogen or halogen, m is 1, 2 or 3 and Y is chlorine, bromine, iodine or the group

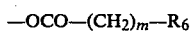

wherein R$_6$ and m have the same significance as above.

A compound of formula VI is reacted with a functional derivative of a lower alkanecarboxylic acid with 1–4 carbon atoms of formula VII. Representative alkanecarboxylic acids include acetic acid and chloroacetic acid. The acylation of the compounds of formula VI is carried out using these functional derivatives of an alkanecarboxylic acid. Such derivatives include the anhydrides such as acetic anhydride, chloroacetic acid anhydride and the like and acid halogenides such as acetyl chloride or chloroacetyl chloride.

The reaction conditions are not critical but are dependent on the carboxylic acid derivative selected as the alkanoylating agent. Room temperature or temperatures above or below room temperature can be used depending on the reagents used with the preferred temperature range being from room temperature to 130° C.

The reaction can be carried out in inert organic solvents, such as hydrocarbons, e.g., benzene, toluene and the like, chlorinated hydrocarbons such as methylene chloride and the like, ethers such as tetrahydrofuran and the like, dimethylformamide and pyridine. Finally, the acylating agent of formula VII can also function as the solvent. When the acylating agent is used as the solvent, small amounts of dimethylformamide should be added to the reaction mixture.

Procedure D

A compound of the formula

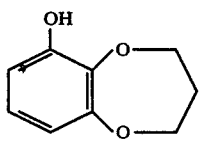

II is reacted with a compound of the formula

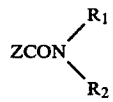

VIII wherein Z is chlorine, bromine or iodine and R$_1$ and R$_2$ are as described in formula I.

The reaction of a compound of formula II with a compound of formula VIII is carried out following standard procedures known conveniently in the art using an excess of the compound of formula VIII and inert organic solvents such as hydrocarbons, e.g., benzene or toluene, chlorinated hydrocarbons, e.g., methylene chloride, ethers, e.g., diethyl ether, and the like. Bases, e.g., potassium carbonate, sodium carbonate, triethylamine, pyridine and the like can be used catalyst. A temperature range of from about 0° C. to the reflux temperature of the reaction mixture can be used with a range of from room temperature to 130° C. preferred.

Procedure E

A compound of the formula

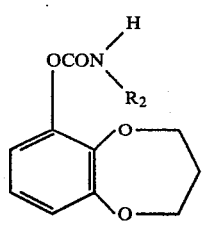

VI is reacted with a lower alkylating, lower alkenylating or lower alkynylating agent.

In this procedure, a compound of formula VI is dissolved in an ether, e.g., dioxan, a di-lower alkyl ketone, e.g., acetone, or dimethylformamide. The resulting mixture is treated with an alkali metal or alkaline earth metal carbonate, preferably sodium carbonate or potassium carbonate. An alkylating agent, alkenylating agent or alkynylating agent is then added. Examples of such agents include the halogenides with the exception of the fluorogenide, alkylsulphonyloxy compounds, preferably mesyloxy derivatives and arylsulphonyloxy compounds, preferably tosyloxy derivatives.

The reaction temperature can range from 0° C. to the boiling point of the reaction mixture with the reflux temperature preferred.

The term "lower alkyl", as used in the instant specification, denotes both straight chain and branched chain hydrocarbon groups containing from 1 to 5 carbon atoms, such as methyl, ethyl, propyl, isopropyl and the like. This is also true for the lower alkyl groups in the radicals such as lower alkylcarbonyl and halogen-lower alkylcarbonyl. The terms "lower alkenyl" and "lower alkynyl" include both straight chain and branched chain hydrocarbon groups containing from 2 to 6 carbon atoms. As examples there may be named: vinyl, allyl, butenyl, pentenyl, ethynyl, propargyl, butynyl. The term "halogen" includes fluorine, chlorine, bromine and iodine. The term "alkali metal" includes lithium, sodium, potassium, rubidium and caesium while the term "alkaline earth metal" includes beryllium, magnesium, calcium, strontium and barium.

Compounds of formula I wherein R$_1$ is lower alkyl of from 1 to 3 carbon atoms are preferred. Such compounds include:

3,4-dihydro-2H-1,5-benzodioxepin-6-yl-(chloroacetyl)-methylcarbamate;

3,4-dihydro-2H-1,5-benzodioxepin-6-yl[(trichloromethyl)thio]-methylcarbamate;

3,4-dihydro-2H-1,5-benzodioxepin-6-yl-N,N-dimethylcarbamate.

Other representative compounds include:

3,4-dihydro-2H-1,5-benzodioxepin-6-yl-allylcarbamate;

3,4-dihydro-2H-1,5-benzodioxepin-6-yl-propargylcarbamate.

An especially preferred compound of this invention is 3,4-dihydro-2H-1,5-benzodioxepin-6-yl methylcarbamate.

The phenylcarbamates of this invention are active as pesticides and, in particular, as insecticides wherein they function both as contact and systemic insecticides. As such they are especially active against house flies, caterpillars and aphids. As pesticides the phenylcarbamates are effective in the control of animal pests and especially for the elimination of ticks. Thus, the term "pesticide" as used herein include insecticides.

The instant invention is also directed to pesticidal compositions which contain, as the active ingredient, mixtures of one or more of the phenylcarbamates of formula I. Since the phenylcarbamates of formula I are active pest control agents, the ratios of the active ingredients in the compositions are not critical.

Further, the present invention is directed to methods of combatting pests which comprises applying these compositions to, and pesticidal treatment of, plants, animals and soil.

Since the phenylcarbamates of formula I are, in general, water-insoluble and in order to effect uniform distribution of the active ingredient of the pesticide compositions according to this invention, the active ingredient can be mixed with adjuvants conventionally used for pesticidal application so that they may be formulated as solutions, emulsions, emulsifiable concentrates, dispersions, dusts or wettable powders. Thus, the pesticidal compositions can contain, for example, carrier material, wetting agents, inert diluents, solvents and the like.

In addition to these adjuvants the pesticidal compositions of this invention can contain other active pesticides, insecticides, bactericides and fungicides in addition to the phenylcarbamates of formula I. Particularly advantageous compositions can be obtained with mixtures with other insecticides.

For example, the phenylcarbamates of formula I can be dissolved in a water-immiscible solvent such as a high-boiling hydrocarbon which contains dissolved emulsifiers so that, upon addition to water, the phenylcarbamate solution acts as a self-emulsifiable oil.

The phenylcarbamates can also be mixed with a wetting agent with or without an inert diluent to form a wettable powder which is soluble or dispersible in water. The active ingredient can also be mixed with inert diluents to form a solid or powdery product.

Inert diluents with which the phenylcarbamates of formula I can be admixed are solid inert materials including powdery or finely divided solid materials such as clays, sands, talc, mica, fertilizers and the like. The resulting compositions can, thus, either be in the form of ducts or can be compositions having a larger particle size.

Wetting agents suitable for use in the pesticidal compositions of this invention can be anionic, non-ionic or cationic.

Examples of anionic wetting agents which can be used in these compositions include soaps, fatty sulfates and cetyl sodium sulfate, fatty-aromatic sulfonates such as alkylbenzenesulfonates and butylnaphthalenesulfonates, complex fatty sulfonates such as the amide condensation product of oleic acid and N-methyl-taurin and the sodium sulfonate of dioctylsuccinate.

Examples of non-ionic wetting agents which can be used in these compositions include, for example, condensation products of fatty acids, fatty alcohols or fat-substituted phenols with ethylene oxide, fatty acid esters and ethers of sugars or polyvalent alcohols or products which are obtained from the latter by condensation with ethylene oxide and the products which are known as block copolymers of ethylene oxide and propylene oxide.

Examples of cationic wetting agents which can be used in these compositions include cetyltrimethylammonium bromide and the like.

The pesticidal compositions of this invention can also be used in the form of an aerosol. Such compositions can contain, in addition to the propellant gas, which is a polyhalogenated alkane such as dichlorodifluoromethane, a co-solvent and a wetting agent.

For the different uses of the phenylcarbamates of this invention, the quantities of active ingredient used can vary. For example, in the treatment of plants for the control of pests thereon, the compounds are used to an extent of about 17–1120 g/ha and preferably in an amount of 35–280 g/ha. In the treatment of animals for the control of ticks, the animal is conveniently dipped in a solution containing 30–300 ppm. of active compound or sprayed with such a solution.

The following Examples illustrate the invention. Unless otherwise indicated, all parts and percentages are by weight.

EXAMPLE 1

63 G. of pyrogallol are dissolved with stirring in 330 ml. of absolute alcohol in a flask under a nitrogen atmosphere. 56 G. of potassium hydroxide are added to the flask and the temperature of the reaction mixture rises to 65° C. To the resulting dark-brown, clear solution, 200 g. of 1,3-dibromopropane are added dropwise a over 30 minute period. The resulting mixture is refluxed overnight with stirring. The mixture is cooled to room temperature and filtered. The ethanolic solution is evaporated to dryness and the residual oil is dissolved in 200 ml. of ether. The ether solution is washed several times with water, dried over sodium sulfate, filtered and evaporated to dryness. A dark oil, 3,4-dihydro-2H-1,5-benzodioxepin-6-ol is obtained. This oil is recrystallized from ether and petroleum ether to yield white crystals, m.p. 112°–114° C.

12.5 G. of 3,4-dihydro-2H-1,5-benzodioxepin-6-ol (0.075 mol) (prepared as described above) are dissolved in 40 ml. of methylene chloride and 2 ml. of methanol and 0.5 g. of potassium carbonate are added to the solution. While this solution is cooled on an ice bath, 6 ml. of methylisocyanate is added in two portions with stirring. The mixture is stirred at room temperature for 2 hours. The solution is then diluted with 50 ml. of methylene chloride, washed with water, dried over sodium sulfate and evaporated to dryness. The resulting 3,4-dihydro-2H-1,5-benzodioxepin-6-yl methylcarbamate is recrystallized from ether/petroleum ether (60°–80° C.), m.p. 127°–128° C.

EXAMPLE 2

11.2 G. of 3,4-dihydro-2H-1,5-benzodioxepin-6-yl methylcarbamate, 100 ml. of toluene and 11.3 g. of chloroacetyl chloride are refluxed for 48 hours and then the mixture is evaporated to dryness. The yellow oil which remains is recrystallized from ether/petroleum ether (40°–45° C.). There is obtained 3,4-dihydro-2H-1,5-benzodioxepin-6-yl(chloroacetyl)methylcarbamate, m.p. 63°–64° C.

EXAMPLE 3

3.3 G. of 3,4-dihydro-2H-1,5-benzodioxepin-6-ol are dissolved in 40 ml. of tetrahydrofuran and 2.33 g. of sodium carbamate are added. The mixture is heated to 40° C. with stirring, 4.3 grams of dimethyl carbamyl chloride in 5 ml. of tetrahydrofuran are added dropwise and the reaction is maintained at a temperature of 60° C. overnight. The reaction mixture is poured onto ice water and this mixture is then extracted three times with ethyl acetate. The extract is washed first with a sodium chloride solution containing one-half the amount of sodium chloride as in a saturated solution and then with a saturated sodium chloride solution, dried over sodium sulfate and evaporated. The residue is chromatographed on 160 g. of silica gel using hexane-ethyl acetate (4:1) as the elution agent. The product obtained is 3,4-dihydro-2H-1,5-benzodioxepin-6-yl-N,N-dimethyl-carbamate, m.p. 46°–47° C.

EXAMPLE 4

1.3 G. of sodium hydride (50% dispersion in oil) are washed twice with petroleum ether (40°–45° C.) and then suspended in 30 ml. of absolute benzene in a flask. 4.15 G. 1,5-benzodioxepin-6-ol (0.025 mol) are added stepwise with stirring and under a nitrogen atmosphere. This mixture is stirred for 30 minutes at room temperature and then a solution of 6.7 g. of N-trichloromethylthio-N-methyl carbamyl chloride (freshly prepared) in 30 ml. of absolute benzene is added over a 30 minute period. The resulting mixture is stirred at room temperature for four hours, then poured into 50 ml. of ice water and extracted three times with 30 ml. of benzene. The benzene extracts are washed with water, dried over sodium sulfate and evaporated. The crude product is chromatographed on silica gel and eluted with dichloromethylene. On evaporation, 3,4-dihydro-2H-1,5-benzodioxepin-6-yl-[(trichloromethyl)thio]-methylcarbamate is obtained as a yellow oil; $M_D^{24}$:1.5658.

EXAMPLE 5

This example illustrates the activity of phenylcarbamates against *Carpocapsa pomella* (apple moth).

Solutions containing the following active ingredients were prepared:

| Solution | Active Ingredient |
|---|---|
| A | 3,4-dihydro-2H-1,5-benzodioxepin-6-yl methylcarbamate |
| B | 3,4-dihydro-2H-1,5-benzodioxepin-6-yl(chloracetyl) methylcarbamate |
| C | 3,4-dihydro-2H-1,5-benzodioxepin-6-yl [(trichloromethyl)thio]-methylcarbamate |

Five apple plugs (calottes) were sprayed with one of the above solutions at a dosage of $10^{-6}$ g. active ingredient/cm$^2$. One hour after spray treatment two freshly hatched larvae of the apple moth were placed on each apple plug. The plugs were then covered with small plastic pots. After 5 days, the pots were removed and the plugs were examined for normally developing larvae.

The results are reported below expressed as the percent reduction in the normally developing larvae as compared to developing larvae on untreated control plugs.

| Solution | % Reduction |
|---|---|
| A | 100 |
| B | 100 |
| C | 100 |

(The mortality of larvae in the untreated controls was 8%.)

EXAMPLE 6

This Example illustrates the activity of phenylcarbamates against *Leptinotassa decamlineata*, potato beetle.

Solutions A, B and C containing the same active ingredients as in Example 5 above were used in this test.

Two potato leaf plots were sprayed with one of the above solutions at a dosage of $10^{-6}$ g. of active ingredient/cm$^2$.

One hour after the spray treatment, five freshly hatched larvae were placed on each leaf plot. The plots were then covered with small plastic pots and kept four days at 25° C. and 60% relative humidity.

The results are reported below as the percent reduction in the survival rate of the larvae on the treated plots as compared to the survival rate on untreated control plots.

| Solution | % Reduction |
|---|---|
| A | 100 |
| B | 100 |
| C | 100 |

(The mortality of larvae on the untreated plots was 5%.)

We claim:

1. A compound represented by the formula wherein $R_1$ is lower alkyl, lower alkenyl, lower alkynyl, lower alkylcarbonyl, halogen-lower alkylcarbonyl or trichloromethylsulfenyl and $R_2$ is hydrogen or lower alkyl.

2. 3,4-dihydro-2H-1,5-benzodioxepin-6-yl-methylcarbamate.

3. 3,4-dihydro-2H-1,5-benzodioxepin-6-yl-(chloracetyl)-methylcarbamate.

4. 3,4-dihydro-2H-1,5-benzodioxepin-6-yl-[(trichloromethyl)thio]-methylcarbamate.

5. 3,4-dihydro-2H-1,5-benzodioxepin-6-yl-allylcarbamate.

6. 3,4-dihydro-2H-1,5-benzodioxepin-6-yl-propargyl-carbamate.

7. 3,4-dihydro-2H-1,5-benzodioxepin-6-yl-N,N-dimethylcarbamate.

8. A pesticidal composition which comprises inert carrier material and, as the active ingredient, an amount, which is effective as a pesticide, of a compound of the formula wherein $R_1$ is lower alkyl, lower alkenyl, lower alkynyl, lower alkylcarbonyl, halogen-lower alkylcarbonyl or trichloromethylsulfenyl and $R_2$ is hydrogen or lower alkyl and mixtures of these compounds.

9. The pesticidal composition of claim 8 wherein the active ingredient is 3,4-dihydro-2H-1,5-benzodioxepin-6-yl-methylcarbamate.

10. The pesticidal composition of claim 8 wherein the active ingredient is 3,4-dihydro-2H-1,5-benzodioxepin-6-yl-(chloroacetyl)-methylcarbamate.

11. The pesticidal composition of claim 8 wherein the active ingredient is 3,4-dihydro-2H-1,5-benzodioxepin-6-yl-[(trichloromethyl)thio]-methylcarbamate.

12. The pesticidal composition of claim 8 wherein the active ingredient is 3,4-dihydro-2H-1,5-benzodioxepin-6-yl-allylcarbamate.

13. The pesticidal composition of claim 8 wherein the active ingredient is 3,4-dihydro-2H-1,5-benzodioxepin-6-yl-propargylcarbamate.

14. The pesticidal composition of claim 8 wherein the active ingredient is 3,4-dihydro-2H-1,5-benzodioxepin-6-yl-N,N-dimethylcarbamate.

15. A method for the control of pests which comprises applying, to the site to be treated, an amount of the pesticidal composition of claim 8 which is effective in the control of pests.

16. The method of claim 15 wherein the active ingredient of the pesticidal composition is 3,4-dihydro-2H-1,5-benzodioxepin-6-yl-methylcarbamate.

17. The method of claim 15 wherein the active ingredient of the pesticidal composition is 3,4-dehydro-2H-1,5-benzodioxepin-6-yl-(chloroacetyl)-methylcarbamate.

18. The method of claim 15 wherein the active ingredient of the pesticidal composition is 3,4-dihydro-2H-1,5-benzodioxepin-6-yl-[(trichloromethyl)thio]-methylcarbamate.

* * * * *